(12) United States Patent
Medoff et al.

(10) Patent No.: US 6,448,307 B1
(45) Date of Patent: *Sep. 10, 2002

(54) COMPOSITIONS OF TEXTURIZED FIBROUS MATERIALS

(75) Inventors: Marshall Medoff, Brookline; Arthur P. Lagace, Newtonville, both of MA (US)

(73) Assignee: Xyleco, Inc., Brookline, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/593,627

(22) Filed: Jun. 13, 2000

Related U.S. Application Data

(63) Continuation-in-part of application No. 09/337,580, filed on Jun. 22, 1999, now Pat. No. 6,207,729, which is a continuation-in-part of application No. 08/961,863, filed on Oct. 31, 1997, now Pat. No. 5,973,035, and a continuation-in-part of application No. 09/338,209, filed on Jun. 22, 1999, which is a continuation-in-part of application No. 08/921,807, filed on Sep. 2, 1997, now Pat. No. 5,952,105.

(51) Int. Cl.$^7$ .................. A01G 13/00; A01N 25/00; A23G 3/00; C08J 89/00; C09K 11/00

(52) U.S. Cl. .................. 523/129; 524/13; 524/14; 524/76; 47/26; 47/65.5; 111/200; 424/405; 424/411; 424/413; 424/414; 424/94.1; 428/364; 428/374; 426/5

(58) Field of Search .................. 523/129; 524/13, 524/14, 76; 47/26, 65.5; 111/200; 424/405, 411, 413, 414, 94.1; 428/364, 374; 426/5

(56) References Cited

U.S. PATENT DOCUMENTS

| | | |
|---|---|---|
| 1,824,221 A | 9/1931 | Mason |
| 2,516,847 A | 8/1950 | Boehm |
| 2,658,828 A | 11/1953 | Pattilloch |
| 2,665,261 A | 1/1954 | Baker |
| 2,757,150 A | 7/1956 | Heritage |
| 3,516,953 A | 6/1970 | Wood |
| 3,718,536 A | 2/1973 | Downs et al. |
| 3,836,412 A | 9/1974 | Boustany et al. |
| 3,943,079 A | 3/1976 | Hamed |
| 4,112,038 A | 9/1978 | Garner |
| 4,113,908 A | 9/1978 | Shinomura |
| 4,204,010 A | 5/1980 | Kramm et al. |
| 4,244,847 A | 1/1981 | Posiviata et al. |
| 4,265,846 A | 5/1981 | Shen et al. |
| 4,279,790 A | 7/1981 | Nakajima |
| 4,318,351 A | 3/1982 | Munk |
| 4,559,376 A | 12/1985 | Kubat |
| 4,608,922 A | 9/1986 | Pohl |
| 4,632,170 A | 12/1986 | Pohl |
| 4,674,414 A | 6/1987 | Nülle et al. |
| 4,717,742 A | 1/1988 | Beshay |
| 4,738,723 A | 4/1988 | Frizzell et al. |
| 4,746,688 A | 5/1988 | Bistak et al. |
| 4,791,020 A | 12/1988 | Kokta |
| 4,810,445 A | 3/1989 | Lamb, Sr. et al. |
| 4,818,604 A | 4/1989 | Tock |
| 4,874,095 A | 10/1989 | Warych |
| 4,963,603 A | 10/1990 | Felegi, Jr. et al. |
| 5,064,692 A | 11/1991 | Hofmann et al. |
| 5,084,135 A | 1/1992 | Brooks et al. |
| 5,088,910 A | 2/1992 | Goforth et al. |
| 5,096,046 A | 3/1992 | Goforth et al. |
| 5,096,406 A | 3/1992 | Brooks et al. |
| 5,100,545 A | 3/1992 | Brooks |
| 5,100,603 A | 3/1992 | Neefe |
| 5,124,519 A | 6/1992 | Roy et al. |
| 5,137,668 A | 8/1992 | Lamb, Sr. |
| 5,155,147 A | 10/1992 | Dietz et al. |
| 5,194,461 A | 3/1993 | Bergquist et al. |
| 5,213,021 A | 5/1993 | Goforth et al. |
| 5,254,617 A | 10/1993 | Inoue et al. |
| 5,268,074 A | 12/1993 | Brooks et al. |
| 5,277,758 A | 1/1994 | Brooks et al. |
| 5,284,610 A | 2/1994 | Tai |
| 5,285,973 A | 2/1994 | Goforth et al. |
| 5,298,102 A | 3/1994 | Pohl |
| 5,351,895 A | 10/1994 | Brooks et al. |
| 5,366,790 A | 11/1994 | Liebel |
| 5,372,878 A | 12/1994 | Saito |
| 5,374,474 A | 12/1994 | Pratt et al. |
| 5,380,180 A | 1/1995 | Lamb, Sr. |
| 5,421,205 A | 6/1995 | Pohl |
| 5,437,766 A | 8/1995 | Van Phan et al. |
| 5,439,542 A | 8/1995 | Liebel |
| 5,441,801 A | 8/1995 | Deaner et al. |
| 5,480,602 A | 1/1996 | Nagaich |
| 5,486,553 A | 1/1996 | Deaner et al. |
| 5,516,472 A | 5/1996 | Laver |
| 5,539,027 A | 7/1996 | Deaner et al. |
| 5,540,244 A | 7/1996 | Brooks et al. |
| 5,543,205 A | 8/1996 | Liebel |

(List continued on next page.)

FOREIGN PATENT DOCUMENTS

| | | |
|---|---|---|
| AU | 47811/90 | 1/1989 |
| EP | 0 161 766 A1 | 11/1985 |
| WO | WO 96/13468 | 5/1996 |
| WO | WO 96/13551 | 5/1996 |
| WO | WO 97/18173 | 5/1997 |

OTHER PUBLICATIONS

Abstract of JP 09213296, filed Feb. 5, 1996, in Chemical Abstracts 127:223004.

Abstract of JP 09267441, filed Oct. 14, 1997, in Chemical Abstracts 127:294599.

Abstract of (Doctorate) Dissertation Abstract Int. B1988, 58(9), 4962 (published in Sep. 1997), in Chemical Abstracts 128:128805.

*Primary Examiner*—Nathan M. Nutter
(74) *Attorney, Agent, or Firm*—Fish & Richardson P.C.

(57) ABSTRACT

The invention is based on the discovery that texturized cellulosic and/or lignocellulosic materials can be combined with many different matrix materials, including organic matrices (e.g., thermosetting resins, elastomers, asphalts, lignins, or tars) to produce useful compositions.

49 Claims, 3 Drawing Sheets

U.S. PATENT DOCUMENTS

| | | |
|---|---|---|
| 5,558,933 A | 9/1996 | Anthony |
| 5,574,094 A | 11/1996 | Malucelli et al. |
| 5,582,682 A | 12/1996 | Ferretti |
| 5,643,359 A | 7/1997 | Soroushian et al. |
| 5,643,635 A | 7/1997 | Ahn et al. |
| 5,746,958 A | 5/1998 | Gustafsson et al. |
| 5,759,680 A | 6/1998 | Brooks et al. |
| 5,767,177 A | 6/1998 | Omente et al. |
| 5,819,491 A | 10/1998 | Davis |
| 5,824,246 A | 10/1998 | Reetz |
| 5,827,607 A | 10/1998 | Deaner et al. |
| 5,851,469 A | 12/1998 | Muller et al. |
| 5,932,334 A | 8/1999 | Deaner et al. |
| 5,948,524 A | 9/1999 | Seethamraju et al. |
| 5,973,035 A * | 10/1999 | Medoff et al. ................ 524/13 |
| 6,004,668 A | 12/1999 | Deaner et al. |
| 6,015,611 A | 1/2000 | Deaner et al. |
| 6,015,612 A | 1/2000 | Deaner et al. |

* cited by examiner

COMPOSITIONS OF TEXTURIZED FIBROUS MATERIALS

CROSS REFERENCE TO RELATED APPLICATIONS

This application is a continuation-in-part of U.S. patent application Ser. No. 09/337,580, filed Jun. 22, 1999, and now issued as U.S. Pat. No. 6,207,729 which is a continuation-in-part of U.S. patent application Ser. No. 08/961,863, filed Oct. 31, 1997, now issued as U.S. Pat. No. 5,973,035; and is a continuation-in-part of U.S. patent application Ser. No. 09/338,209, filed Jun. 22, 1999, which is a continuation-in-part of U.S. patent application Ser. No. 08/921,807, filed Sep. 2, 1997, now issued as U.S. Pat. No. 5,952,105.

BACKGROUND OF THE INVENTION

The invention relates to compositions containing texturized fibrous materials prepared from cellulosic and/or lignocellulosic materials, including but not limited to poly-coated paper, and a matrix material.

Cellulosic and lignocellulosic materials are produced, processed, and used in large quantities in a number of applications. Once used, these fibers are usually discarded as waste materials. As a result, there is an ever-increasing amount of waste cellulosic and lignocellulosic fiber. Paper coated with a polymer (poly-coated paper) is used in a number of applications. For example, poly-coated paper is used to make a variety of food containers, including juice cartons and boxes for frozen foods.

SUMMARY OF THE INVENTION

The invention is based on the discovery that texturized cellulosic and/or lignocellulosic materials can be combined with many different matrix materials, including organic matrices (e.g., thermosetting resins, elastomers, asphalts, lignins, or tars) to produce useful compositions.

In one embodiment, the invention features a composition that includes a matrix reinforced with at least about 2% fiber (e.g., 2%, 5%, 10%, 30%, 50%, 70%, 90% or more, e.g., 10 to 90%, e.g., 30 to 70%), where the fiber is a lignocellulosic or cellulosic material that has been sheared to the extent that the internal fibers are substantially exposed. Material thus sheared is termed "texturized." At least 5% (e.g., 5% 10%, 5%, 10%, 25%, 50%, 75%, 90%, 95%, 99%, or substantially all) of the material by weight can be texturized. Generally, at least about 5% or 10%, more preferably at least about 25%, 50%, or 70%, of these fibers have a length/diameter (L/D) ratio of at least 5, more preferably at least 10 or 25, or at least 50.

The matrix can include, for example, a thermosetting resin (e.g., an alkyd, a diallyl phthalate, an epoxy, a melamine, a phenolic, a silicone, a urea, a thermosetting polyester, or their derivatives, or a combination of two or more such thermoplastic resins), an elastomer (e.g., natural rubber, isoprene rubber, styrene-butadiene copolymers, neoprene, nitrile rubber, butyl rubber, ethylene propylene copolymer ("EPM"), ethylene propylene diene terpolymer ("EPDM"), hypalon, acrylic rubber, polysulfide rubber, silicones, urethanes, fluoroelastomers, butadiene, or epichlorohydrin rubber, or combinations or derivatives thereof), a tar or asphalt, or a lignin (e.g., lignins that have been extracted and/or isolated and/or purified from their natural sources, or synthetic or modified lignins and their derivatives). The matrix can be prepared from natural or synthetic components, or combinations of both.

The composition can also include optional additives such as pharmaceuticals; agricultural compounds; enzymes; particulate, powdered, or granulated solids; plant seeds; foodstuffs (e.g., for human consumption or animal feed); bacteria; and/or additives such as calcium carbonate, graphite, asbestos, wollastonite, mica, glass, fiber glass, chalk, talc, silica, ground construction waste, tire rubber powder, carbon fibers, metal fibers, plasticizers, lubricants, antioxidants, opacifiers, heat stabilizers, colorants, impact modifiers, photostabilizers, biocides, antistatic agents, organic or inorganic flame retardants, biodegradation agents, dispersants, emulsion polymers, accelerators, extenders, retardants, antifoaming agents, thixotropic agents, or waterproofing agents. In some cases, such additives can constitute from about 0.5% to about 20% (e.g., 0.5%, 1%, 2%, 5%, 10%, 15%, or 20%), or more, of the total weight of the composition.

The composition can be in a bulk form, or can be in the form of articles such as pipes, panels, decking materials, boards, housings, sheets, blocks, bricks, pebbles, stones, poles, straps, fencing, members, doors, shutters, awnings, shades, signs, frames, window casings, backboards, flooring, tiles, railroad ties, forms, trays, tool handles, stalls, bedding, dispensers, staves, films, wraps, tapes, bands, totes, barrels, boxes, packing materials, baskets, straps, slips, racks, casings, binders, dividers, walls, indoor and outdoor carpets, rugs, woven goods, mats, frames, bookcases, sculptures, chairs, tables, desks, art, toys, games, pallets and other materials handling systems, wharves, piers, boats, masts, pollution control products, gravel, paving materials, road beds, swimming pools, septic tanks, automotive panels, substrates, computer housings, above- and below-ground electrical casings, furniture, picnic tables, tents, playgrounds, benches, shelters, sporting goods, beds, bedpans, thread, filament, cloth, plaques, trays, hangers, servers, pools, insulation, caskets, book covers, clothes, canes, crutches, and other construction, agricultural, material handling, transportation, automotive, industrial, environmental, naval, electrical, electronic, recreational, medical, textile, and consumer products, rubber hoses, marine products, pipes, or polymeric foams.

The term "texturized fibrous material", as used herein, refers to cellulosic or lignocellulosic material that has been sheared to the extent that its internal fibers are substantially exposed. Generally, at least about 10%, more preferably at least about 25%, 50%, or 70%, of these fibers have a length/diameter (L/D) ratio of at least 5, more preferably at least 10 or 25, or at least 50. An example of texturized fibrous newsprint is shown in FIG. 1. An example of texturized poly-coated paper is shown in FIG. 2.

The term "matrix", as used herein, refers to the continuous phase of the compositions described herein and can include, for example, thermoplastic resins, thermosetting resins, elastomers, tars, lignins, or asphalts, or mixtures of any of these or other materials. Other components (e.g., contaminants, metal filings) may also be present in the matrix.

The term "thermosetting resin", as used herein, refers to plastics (e.g., organic polymers) that are cured, set, or hardened into a permanent shape. Curing is an irreversible chemical reaction typically involving molecular cross-linking using heat or irradiation (e.g., UV irradiation). Curing of thermosetting materials can be initiated or completed at, for example, ambient or higher temperatures. The cross-linking that occurs in the curing reaction is brought about by the linking of atoms between or across two linear polymers, resulting in a three-dimensional rigidified chemical structure.

Examples of thermosetting resins include, but are not limited to, silicones, alkyds, diallyl phthalates (allyls), epoxies, melamines, phenolics, certain polyesters, silicones, ureas, polyurethanes, polyolefin-based thermosetting resins such as TELENE™ (BF Goodrich) and METTON™ (Hercules).

The term "elastomer", as used herein, refers to macromolecular materials that rapidly return to approximate their initial dimensions and shape after deformation and subsequent release.

Examples of elastomers include, but are not limited to, natural rubber, isoprene rubber, styrene-butadiene copolymers, neoprene, nitrile rubber, butyl rubber, ethylene propylene copolymer (i.e., "EPM") and ethylene propylene diene terpolymer (i.e., "EPDM"), hypalon, acrylic rubber, polysulfide rubber, silicones, urethanes, fluoroelastomers, butadiene, and epichlorohydrin rubber.

The term "tar", as used herein, means a typically thick brown to black liquid mixture of hydrocarbons and their derivatives obtained by distilling wood, peat, coal, shale, or other vegetable or mineral materials. An example is coal tar, which is made by destructive distillation of bituminous coal or crude petroleum (e.g., containing naphthalene, toluene, quinoline, aniline, and cresols).

The term "lignin", as used herein, refers to an amorphous substance, mixture, or powder isolated from wood, plants, recycled wood or plant products, or as a byproduct of paper making. In nature, lignins, together with cellulose, form the woody cell walls of plants and the cementing material between them. They are typically polymeric and may be distinguished from cellulose by (1) a higher carbon content than cellulose, and (2) the inclusion of propyl-benzene units, methoxyl groups, and/or hydroxyl groups. They are generally not hydrolyzed by acids but may be soluble in hot alkali and bisulfite, and may be readily oxidizable. Lignins can be recovered from the liquor that results from the sulfate or soda process of making cellulosic pulp, or from sulfite liquor. The term lignin thus includes sulfite lignin, or ligninsulfonates.

The term "asphalt", as used herein, refers, for example, to an amorphous, solid, or semisolid mixture of hydrocarbons, brownish-black pitch, or bitumen, produced from the higher-boiling point minerals oils by the action of oxygen. Asphalts include both asphaltenes and carbenes. Asphalts are commonly used for paving, roofing, and waterproofing materials.

The new compositions have properties that render them useful for various applications. Compositions that include texturized fibrous material and matrices are, for example, strong, lightweight, and inexpensive.

Other advantages afforded by the texturized fibers include:

(1) Reduced densities of matrix materials such as elastomers and thermosetting resins.

(2) Higher impact resistance due to increased interfacial area between matrix and texturized fiber and increased energy absorbed when texturized fiber delaminates from matrices.

(3) Reduced surface friction.

(4) Higher lubricity surfaces.

(5) Enhanced tolerance for and compatibilization of both the hydrophobic and hydrophilic constituents in the matrices.

(6) Enhanced ability to custom tailor the properties of the composition for specific requirements.

Other features and advantages of the invention will be apparent from the following detailed description, and from the claims.

DETAILED DESCRIPTION OF THE INVENTION

Figure 1:
FIG. 1 is a photograph of a texturized newspaper, magnified fifty times.

The invention is directed to compositions that include texturized cellulosic and/or lignocellulosic materials, combined with many different matrix materials, including organic matrices (e.g., thermosetting resins, elastomers, asphalts, lignins, or tar-like materials).

Examples of cellulosic fiber include paper and paper products such as newsprint and effluent from paper manufacture, as well as materials derived from kenaf, grasses, rice hulls, bagasse, cotton, jute, other stem plants (e.g., hemp, flax, bamboo; both bast and core fibers), leaf plants (e.g., sisal, abaca), and agricultural fibers (e.g., cereal straw, corn cobs, rice hulls, and coconut hair). Examples of lignocellulosic fiber include wood, wood fibers, and wood-related materials.

In addition to virgin materials, post-consumer, industrial, and processing waste can also be used as fiber sources. For example, scrap, waste, or recycled poly-coated paper can be used as a fiber source.

The fibers can optionally be chemically treated, for example, with silanes, stearates, surfactants, or other compounds to render them lipophilic, lipophobic, more adherent, and/or dispersible or processable for a given product application (e.g., within polymeric, elastomeric, tar, asphalt, or lignin matrices). Other additives, or mixtures of matrix materials, can also be used.

The mechanical properties of matrices are influenced by the condition of the reinforcing fiber and the quality of the preparation process. In general, the greater the fiber length in the product, the higher certain mechanical moduli will be. The fiber-to-matrix weight ratio in the final product can also affect mechanical properties (e.g., tensile strength, flexural strength, and/or compressive strength). Texturized fiber has the advantage of having lower specific gravity than traditional reinforcing materials such as glass fiber, resulting in strong, lightweight, economical products.

The resulting compositions include a network of fibers, encapsulated within a matrix. The fibers are thought to form a lattice network, which provides the composition with strength. Since the cellulosic and/or lignocellulosic material is texturized, the amount of surface area available to bond to the matrices increased, in comparison with compositions prepared with un-texturized cellulosic or lignocellulosic material. The matrix material binds to the surface of the exposed fibers, creating an intimate blend of the fiber network and the resin matrix. The intimate blending of the fibers and the matrix further strengthens the compositions.

Preparation of Texturized Fiber

If scrap cellulosic or lignocellulosic fiber is used, it should be cleaned and dried. The fiber can be texturized using any one of a number of mechanical means, or combinations thereof. One method of texturizing includes first cutting the cellulosic or lignocellulosic fiber into ¼- to ½-inch pieces, if necessary, using a standard cutting apparatus (e.g., including a rotary cutter having fixed blade knives and 12–48" rotating blades, which can be either segmented with ¼" to ½" segments, or continuous).

Counter-rotating screw shredders and segmented rotating screw shredders such as those manufactured by Munson (Utica, N.Y.) can also be used, as can a standard document shredder as found in many offices.

The cellulosic or lignocellulosic fiber is then sheared with a rotary cutter, such as the one (available from Sprout, Waldron Companies) described in Perry's Chem. Eng. Handbook, 6th Ed., at pp. 8–29 (1984). Although other settings can be used, the spacing between the rotating knives and bed knives of the rotary cutter is typically set to 0.002" or less, and blade rotation is set to 1750 rpm or more. The rotary cutter can be cooled to 100° C. or lower during the process, for example, using a water jacket.

The texturized fiber can be passed through a discharge screen. Larger screens (e.g., up to 6 mm) can be used in large-scale production. The paper is generally kept in contact with the blades of the rotary cutter until the fibers are pulled apart; smaller screens (e.g., 2 mm mesh) provide longer residence times, but can result in lower length/diameter (L/D) aspect ratios. A vacuum drawer can be attached to the screen to maximize and maintain fiber length/diameter aspect ratio.

For certain applications, drying of the fibers is useful. Prior to combination with matrix materials, the texturized fiber can be stored in sealed bags (i.e., to reduce the amount of subsequent drying required), and then dried at approximately 105° C. for 4–18 hours (until the moisture content is less than about 0.5%) immediately before use.

Compositions of Texturized Fibrous Material

Compositions containing texturized fibrous material and matrices of thermosetting resins, elastomers, tars, lignins, or asphalts can be used in the manner of other fiber-reinforced materials, for example, for unidirectional or multi-directional reinforcement, and for improved impact resistance, mechanical integrity after impact, stiffness-to-weight ratio, strength-to-weight ratio, stiffness per unit cost, strength per unit cost, overall cost efficiency, weight reduction, and other benefits.

The flexibility of the texturized fiber is a great advantage in that the fibers generally do not substantially break and/or shorten during any of the utilized mixing operations. In addition, the fibers are less abrasive than, for example, certain inorganic fibers, resulting in less wear and tear to the mixing equipment and other process-related equipment.

The texturized fibrous material provides the composition with strength. The composition can, for example, include from about 10% to about 90%, more preferably from about 30% to about 70%, of the texturized fibrous material by weight.

The thermosetting resin, elastomeric, tar, lignin, or asphalt matrices encapsulate the texturized fibrous material and help control the shape of the compositions. The matrices also transfer external loads to the fibrous material and protect the fibers from environmental and structural damage. Compositions can include, for example, about 10% to about 90%, more preferably about 30% to about 70%, by weight, of the matrix materials.

These compositions can also include inorganic additives such as calcium carbonate, graphite, asbestos, wollastonite, mica, glass, fiber glass, chalk, silica, talc, flame retardants such as alumina trihydrate or magnesium hydroxide, ground construction waste, tire rubber powder, carbon fibers, or metal fibers (e.g., aluminum, stainless steel). These additives may reinforce, extend, change electrical or mechanical or compatibility properties, and may provide other benefits. When such additives are included, they may be present in loadings by weight from below 1% to as high as 80%. Typical loadings ranges are between 0.5% and 50% by weight.

Polymeric and elastomeric compositions can also include coupling agents. The coupling agents help to bond the hydrophilic fibers of the texturized fibrous material to the resins.

The compositions having thermosetting or elastomer matrices can also contain additives known to those in the art of compounding, such as plasticizers; lubricants; antioxidants; opacifiers; heat stabilizers; colorants; impact modifiers; photostabilizers; biocides; antistatic agents; organic or inorganic flame retardants, biodegradation agents; and dispersants. Special fiber surface treatments and additives can be used when a specific formulation requires specific property improvement.

Preparation of Compositions of Texturized Fibrous Material and Matrices

The following are non-limiting examples of compositions:

Thermosetting Resins: Compositions of texturized fibrous material and thermosetting resins can be prepared as bulk molding compounds (BMCs), sheet molding compounds (SMCs), or as other formulations.

Bulk molding compounds (BMCs) are materials made by combining a resin and chopped fibers in a dough mixer, then mixing until the fibers are well wetted and the material has the consistency of modeling clay. Most BMCs are based on polyesters, but vinyl esters and epoxies are sometimes used. A pre-weighed amount of the compound is placed in a compression mold, which is then closed and heated under pressure to crosslink the thermosetting polymer. Many electrical parts are made using BMC compounds and processing. Other applications include microwave dishes, table tops, and electrical insulator boxes.

Sheet molding compounds (SMCs) are made by compounding a polyester resin with fillers, pigments, catalysts, mold release agents, and/or special thickeners that react with the polymer to greatly increase the viscosity. The resin mixture is spread onto a moving nylon film. The resin passes under feeders which disperse the texturized fibers. A second film is placed on top, sandwiching the compound inside. The material then passes through rollers that help the resin to wet the fibers, and the material is rolled up. Prior to use, the nylon films are removed and the compound is molded.

Other techniques and preparation procedures can be used to prepare and cure thermosetting systems.

Elastomers: Compositions of texturized fibrous material and elastomers can be prepared by known methods. In one method, for example, the elastomer is added to a rubber/plastic compounding two-roll mill. After a couple of minutes, the other ingredients, including a vulcanizing agent, are added to the roll mill. Once the elastomer has been compounded, the texturized fibrous material is added to the roll mill. The texturized fibrous material is added over a period of about 10 minutes. The compounded material is removed from the roll mill and cut into sheets. It is then compression molded into the desired shape using standard compression molding techniques.

Alternatively, a mixer, such as a Banbury internal mixer or appropriate twin or single screw compounder can be used. If a Banbury mixer is used, the compounded mixture can, for example, be discharged and dropped onto a roll mill for sheeting. Single or twin screw compounders produce a sheet as an extrudate. The mixture can then be compression molded. Likewise, single- or twin-screw compounders can extrude a shaped profile that can be directly vulcanized. The composition can be molded, extruded, compressed, cut, or milled.

Uses of the Compositions of Texturized Fibrous Materials and Matrices

The fiber/matrix compositions can be used in a number of applications. The compositions can be used, for example, as the base or carcass for a veneer product, or sandwiched between layers of paper or other material. Moreover, the compositions can be, for example, surface treated, grooved, milled, shaped, imprinted, textured, compressed, punched, or colored. The surface of the compositions can be smooth or rough.

Compositions containing texturized fibrous material and thermosetting resins, elastomers, tars, lignins, or asphalts can be used, for example, as pipes, panels, decking materials, boards, housings, sheets, blocks, bricks, pebbles, stones, poles, straps, fencing, members, doors, shutters, awnings, shades, signs, frames, window casings, backboards, flooring, tiles, railroad ties, forms, trays, tool handles, stalls, bedding, dispensers, staves, films, wraps, tapes, bands, totes, barrels, boxes, packing materials, baskets, straps, slips, racks, casings, binders, dividers, walls, indoor and outdoor carpets, rugs, woven goods, mats, frames, bookcases, sculptures, chairs, tables, desks, art, toys, games, pallets and other materials handling systems, wharves, piers, boats, masts, pollution control products, gravel, paving materials, road beds, swimming pools, septic tanks, automotive panels, substrates, computer housings, above- and below-ground electrical casings, furniture, picnic tables, tents, playgrounds, benches, shelters, sporting goods, beds, bedpans, thread, filament, cloth, plaques, trays, hangers, servers, pools, insulation, caskets, book covers, clothes, canes, crutches, and other construction, agricultural, material handling, transportation, automotive, industrial, environmental, naval, electrical, electronic, recreational, medical, textile, and consumer products, rubber hoses, marine products (e.g., hulls, boards, slabs, blocks) pipes, and polymeric foams. These or other products can optionally include adhesives on one or more sides or faces, to allow the products to be adhered to walls or floors, for example, or to the surface of other products. Other articles are also contemplated.

The following examples illustrate certain embodiments and aspects of the present invention and are not to be construed as limiting the scope thereof.

EXAMPLES

Example 1

Figure 3:
FIG. 3 is a photograph of a half-gallon polyboard juice carton.

A 1500 pound skid of virgin, half-gallon juice cartons made of polycoated white kraft board was obtained from International Paper. One such carton is shown in FIG. 3. Each carton was folded flat.

The cartons were fed into a 3 hp Flinch Baugh shredder at a rate of approximately 15 to 20 pounds per hour. The shredder was equipped with two rotary blades, each 12" in length, two fixed blades, and a 0.3" discharge screen. The gap between the rotary and fixed blades was 0.10".

Figure 4:
FIG. 4 is a photograph of shredded half-gallon polyboard juice cartons.

A sample of the output from the shredder, consisting primarily of confetti-like pieces, about 0.1" to 0.5" in width and about 0.25" to 1" in length, is shown in FIG. 4. The shredder output was fed into a Thomas Wiley Mill Model 2D5 rotary cutter. The rotary cutter had four rotary blades, four fixed blades, and a 2 mm discharge screen. Each blade was approximately 2" long. The blade gap was set at 0.020".

Figure 2:
FIG. 2 is a photograph of texturized poly-coated paper, magnified fifty times.
Figure 5:
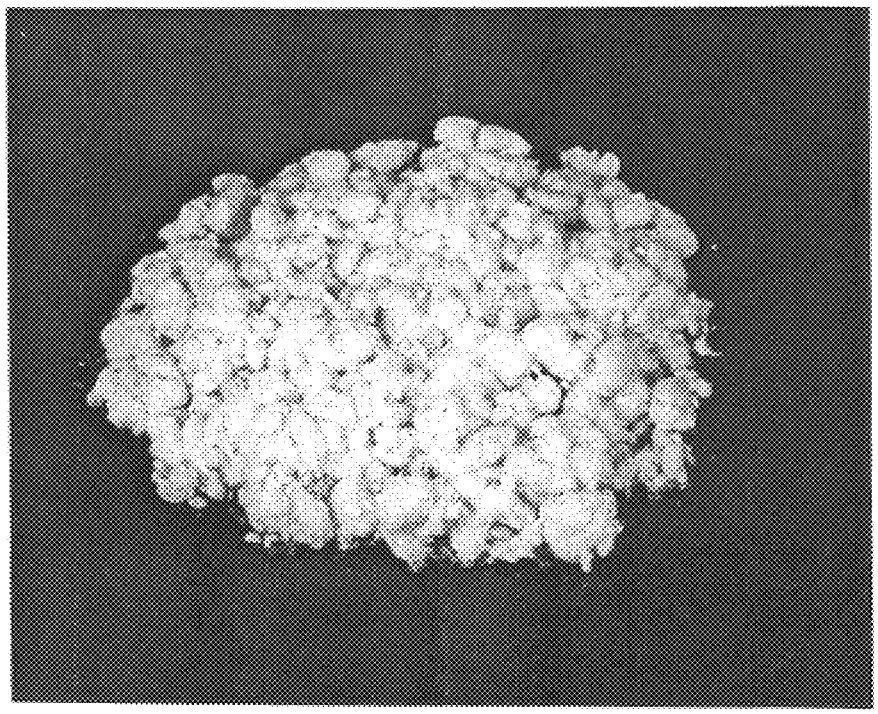
FIG. 5 is a photograph of texturized fibrous material prepared by shearing the shredded half-gallon polyboard juice cartons of FIG. 4.

The rotary cutter sheared the confetti-like pieces across the knife edges, tearing the pieces apart and releasing a finely texturized fiber at a rate of about one pound per hour. The fiber had an average minimum L/D ratio of between five and 100 or more. The bulk density of the texturized fiber was on the order of 0.1 g/cc. A sample of texturized fiber is shown in FIG. 5 at normal magnification, and in FIG. 2 at fifty-fold magnification.

Example 2

Foamed epoxies are used in thermal insulation applications where superior water resistance and elevated temperature properties are desired. Such epoxies can be reinforced with texturized fiber prepared according to the procedure in Example 1. Fillers such as calcium carbonate may optionally be used to obtain some cost reductions. However, overloading with filler can weaken the strength of the foam cell walls, particularly when the foam densities are in the range of five pounds per cubic foot or less, since such low foam density can result in thin, fragile walls within the foam. Filler loadings are generally in the four to five pounds/hundred weight (phr) of resin. Reinforcing with texturized fiber can also provide for reduced weight and cost. In addition, improved strength can be realized because of the high length-to-diameter (L/D) ratios of the texturized fiber. It is not unreasonable to employ up to 30 phr of the fiber. A typical formulation includes:

| Ingredient | Parts |
| --- | --- |
| DGEBA (diglycidyl ether, of bisphenol A) | 100 |
| MPDA ($_m$-phenylenediamine) | 10 |
| Celogen ® ($_{p,p}$-oxybis-benzenesulfonylhydrazide) (Uniroyal Chemical Company) | 10 |
| Surfactant | 0.15 |
| Styrene Oxide | 5 |
| Texturized Fiber | 30 |

This formulation is mixed using standard epoxy mixing techniques. It produces a very high exotherm at the curing temperature of 120° C. and a foam density of about seven pounds per cubic foot.

Other embodiments are within the claims.

What is claimed is:

1. A composition comprising a matrix reinforced with at least about 2% fiber, wherein the fiber is a lignocellulosic or cellulosic material that has been sheared to the extent that the internal fibers are substantially exposed, and wherein the matrix comprises a continuous phase selected from the group consisting of thermoplastic resins, thermosetting resins, elastomers, tars, lignins, asphalts, and mixtures thereof.

2. The composition of claim 1, wherein the matrix comprises a thermosetting resin.

3. The composition of claim 1, wherein the matrix comprises an elastomer.

4. The composition of claim 1, wherein the matrix comprises tar or asphalt.

5. The composition of claim 1, wherein the matrix comprises lignin.

6. The composition of claim 1, further comprising an additive selected from the group consisting of a pharmaceutical; an agricultural compound; an enzyme; a particulate, powdered, or granulated solid; plant seed; a foodstuff; and bacteria.

7. The composition of claim 2, wherein the thermosetting resin is selected from the group consisting of alkyds, diallyl phthalates, epoxies, melamines, phenolics, silicones, ureas, and thermosetting polyesters.

8. The composition of claim 1, wherein at least about 5% by weight of the fibrous material is texturized.

9. The composition of claim 1, wherein the composition comprises about 10% to about 90% by weight texturized fibrous material.

10. The composition of claim 1, wherein the composition comprises about 30% to about 70% by weight texturized fibrous material.

11. The composition of claim 1, further comprising an additive selected from the group consisting of calcium carbonate, graphite, asbestos, wollastonite, mica, glass, fiber glass, chalk, talc, and silica.

12. The composition of claim 7, wherein the additive comprises from about 0.5% to about 20% of the total weight of the composition.

13. The composition of claim 1, wherein said composition is in the form of an article selected from the group consisting of pipes, poles, staves, and masts.

14. The composition of claim 1, wherein at least about 5% of the fibers have a length/diameter ratio of at least about 5.

15. The composition of claim 1, wherein at least about 10% of the fibers have a length/diameter ratio of at least about 5.

16. The composition of claim 1, wherein at least about 25% of the fibers have a length/diameter ratio of at least about 5.

17. The composition of claim 1, wherein at least about 50% of the fibers have a length/diameter ratio of at least about 5.

18. The composition of claim 1, wherein at least about 50% of the fibers have a length/diameter ratio of at least about 25.

19. The composition of claim 1, wherein at least about 50% of the fibers have a length/diameter ratio of at least about 50.

20. The composition of claim 1, wherein at least about 70% of the fibers have a length/diameter ratio of at least about 50.

21. The composition of claim 1, further comprising an additive selected from the group consisting of ground construction waste and tire rubber powder.

22. The composition of claim 1, further comprising carbon fibers.

23. The composition of claim 1, further comprising metal fibers.

24. The composition of claim 1, further comprising a plasticizer.

25. The composition of claim 1, further comprising a lubricant.

26. The composition of claim 1, further comprising an antioxidant.

27. The composition of claim 1, further comprising an opacifier.

28. The composition of claim 1, further comprising a heat stabilizer.

29. The composition of claim 1, further comprising a colorant.

30. The composition of claim 1, further comprising an impact modifier.

31. The composition of claim 1, further comprising a photostabilizer.

32. The composition of claim 1, further comprising a biocide.

33. The composition of claim 1, further comprising an antistatic agent.

34. The composition of claim 1, further comprising a flame retardant.

35. The composition of claim 1, further comprising a biodegradation agent.

36. The composition of claim 1, further comprising a dispersant or an emulsion polymer.

37. The composition of claim 1, further comprising an accelerator.

38. The composition of claim 1, further comprising an extender.

39. The composition of claim 1, further comprising an antifoaming agent.

40. The composition of claim 1, further comprising a thixotropic agent.

41. The composition of claim 1, further comprising a waterproofing agent.

42. The composition of claim 1, wherein said composition is in the form of an article selected from the group consisting of panels, decking materials, boards, sheets, awnings, shades, plaques, dividers, walls, doors, signs, construction products, backboards, flooring, tiles, and automotive panels.

43. The composition of claim 1, wherein said composition is in the form of an article selected from the group consisting of blocks, bricks, pebbles, stones, bedding, gravel, paving materials, and road beds.

44. The composition of claim 1, wherein said composition is in the form of an article selected from the group consisting of straps, films, wraps, tapes, bands, and book covers.

45. The composition of claim 1, wherein said composition is in the form of an article selected from the group consisting of indoor and outdoor carpets, rugs, woven goods, mats, insulation, thread, textile products, clothes, filament, and cloth.

46. The composition of claim 1, wherein said composition is in the form of an article selected from the group consisting of housings, fencing, members, frames, window casings, forms, trays, stalls, dispensers, totes, barrels, boxes, packing materials, baskets, slips, racks, casings, binders, frames, bookcases, pallets and other materials handling systems, wharves, piers, swimming pools, septic tanks, substrates, computer housings, above- and below-ground electrical casings, tents, shelters, bedpans, trays, servers, pools, and caskets.

47. The composition of claim 1, wherein said composition is in the form of an article selected from the group consisting of pollution control products, agricultural products, environmental products, naval products, marine products, automotive products, transportation products, recreational products, industrial products, electrical products, electronic products, medical products, and consumer products.

48. The composition of claim 1, wherein said composition is in the form of an article selected from the group consisting of shutters, railroad ties, tool handles, sculptures, chairs, tables, desks, art, toys, games, boats, beds, furniture, picnic tables, playgrounds, benches, sporting goods, hangers, canes, crutches, and rubber hoses.

49. The composition of claim 1, wherein said composition is in the form of a polymeric foam.

* * * * *